(12) United States Patent  (10) Patent No.: US 8,283,377 B2
Lin et al. (45) Date of Patent: Oct. 9, 2012

(54) METHOD FOR INHIBITING BLOOD VESSEL STENOSIS

(75) Inventors: Shinn-Zong Lin, Taichung (TW); Horng-Jyh Harn, New Taipei (TW); Tzyy-Wen Chiou, Hualien (TW); Li-Fu Chang, Kaohsiung (TW)

(73) Assignee: China Medical University, Taichung (TW)

( * ) Notice: Subject to any disclaimer, the term of this patent is extended or adjusted under 35 U.S.C. 154(b) by 47 days.

(21) Appl. No.: 13/112,220

(22) Filed: May 20, 2011

(65) Prior Publication Data

US 2012/0208875 A1 Aug. 16, 2012

(30) Foreign Application Priority Data

Feb. 15, 2011 (TW) .............................. 00104878 A

(51) Int. Cl.
*A61K 31/365* (2006.01)
*A61P 9/10* (2006.01)
*A61P 9/00* (2006.01)

(52) U.S. Cl. ..................................................... 514/470
(58) Field of Classification Search .................. 514/470
See application file for complete search history.

(56) References Cited

U.S. PATENT DOCUMENTS
2007/0134351 A1 6/2007 Luo et al.

FOREIGN PATENT DOCUMENTS
| TW | 234086 | 4/1993 |
| TW | 403050 | 8/1995 |
| TW | 390876 | 5/1996 |
| TW | 391964 | 5/1996 |

OTHER PUBLICATIONS

Casscells, W., "Migration of smooth muscle and endothelial cells. Critical events in restenosis," Circulation Journal of the American Heart Association, 1992 vol. 86, pp. 723-729.

*Primary Examiner* — San-Ming Hui
*Assistant Examiner* — Kathrien Cruz
(74) *Attorney, Agent, or Firm* — Ping Wang; Andrews Kurth, LLP

(57) ABSTRACT

Provided is a method for inhibiting blood vessel stenosis in a subject, comprising administrating to the subject an effective amount of an active ingredient selected from a group consisting of a compound of formula (I), a pharmaceutically acceptable salt of the compound, a pharmaceutically acceptable ester of the compound, and combinations thereof. Also provided is a method for inhibiting blood vessel stenosis in a subject, comprising administration to the subject an effective amount of an *Angelicae Sinensis* extract comprising the compound of formula (I).

(I)

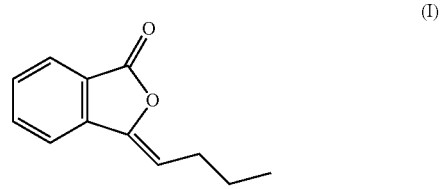

12 Claims, 7 Drawing Sheets

*There is a significant difference when *p value* is <0.05.

* Compared to the Sham group, there is a significant difference when $p\ value$ is <0.05.

Sham (n=6)

n-BP 60 mg/kg (n=6)

n-BP 150 mg/kg (n=6)

n-BP 300 mg/kg (n=6)

*p value <0.05, **p value <0.01

*p value <0.05, **p value <0.01

METHOD FOR INHIBITING BLOOD VESSEL STENOSIS

CROSS-REFERENCES TO RELATED APPLICATIONS

This application claims the benefit of Taiwan Patent Application No. 100104878, filed on Feb. 15, 2011 in the Taiwan Intellectual Property Office, the disclosure of which is incorporated herein in its entirety by reference.

FIELD

The present invention relates to the use of n-butylidenephthalide in inhibiting blood vessel stenosis.

BACKGROUND

Cardiovascular disease is the third highest among the ten leading causes of death for people in Taiwan, following cancer and cerebrovascular disease. Coronary atherosclerosis isone of the main factors that cause cardiovascular disease and is a slow and complicated process. The reason for such occurrence includes the migration of smooth muscle cells to the cardiovascular intimal layer and smooth muscle cell proliferation. This narrows and blocks the blood vessel and leads to myocardial ischemia, myocardial necrosis (myocardial infarction), angina pain (angina pectoris), or even leads to heart failure, cardiogenic shock, or sudden cardiac death.

Cardiovascular disease can be treated by pharmaceutical drugs. Common pharmaceutical drugs include anticoagulants (such as Coumadin), antiplatelet agents (such as aspirin), vasodilators (such as Isordil), hypolipidemic drugs (such as Statins), etc. However, the effect of the drug therapy is slow and limited, and therefore, patients with more severe symptoms are in general treated in combination with surgery. The most commonly seen surgery includes balloon angioplasty, stent implantation, and coronary artery bypass surgery. Balloon angioplasty often is used in conjunction with stent implantation. However, the process of the balloon angioplasty and stent implantation, as well as the balloon and stent themselves, can damage the blood vessel, which leads to inflammation of the blood vessel tissue and the release of cytokines and growth factors, causing smooth muscle cells to migrate to the blood vessel intimal layer and proliferate, and thus results in blood vessel restenosis. Blood vessel restenosis not only greatly reduces the surgery treating effect but also exacerbates the symptom of cardiovascular stenosis. Thus, there is still a need for a method or drug to inhibit cardiovascular stenosis effectively or even inhibit cardiovascular restenosis after surgery in the treatment of cardiovascular diseases to solve various problems that exist with the known therapeutical method.

During the research and development (R&D) of cardiovascular drugs, cell tests or in vitro tests are usually first performed to screen out a compound with the most medicinal potential to obtain a preliminary successful R&D result in this stage. However, it is well-known that in most circumstances, the compound with the most medicinal potential usually cannot pass the following in vivo tests in the animal body, and thus the compound cannot be used in clinical treatment. Hence, despite the numerous compounds that have been deemed to have treatment effects for cardiovascular diseases (such as those disclosed in Taiwan Patent Publication No. 234086, No. 390876, No. 391964, and No. 403650, etc., which are incorporated hereinto by reference), only few cardiovascular drugs can be really used clinically in the market. This explains why the preliminary result of in vitro tests cannot guarantee to obtain the same successful result as in vivo tests.

The inventors of the present invention found that through the in vivo tests, n-butylidenephthalide can effectively inhibit the growth of smooth muscle cells in the animal body, and further inhibit cardiovascular stenosis, or even inhibit the restenosis after surgery. Therefore, n-butylidenephthalide can be used to treat cardiovascular diseases.

SUMMARY

The primary objective of the present invention is to provide a method for inhibiting blood vessel stenosis in a subject, comprising administrating to the subject an effective amount of an active ingredient selected from a group consisting of a compound of formula (I), a pharmaceutically acceptable salt of the compound, a pharmaceutically acceptable ester of the compound, and combinations thereof:

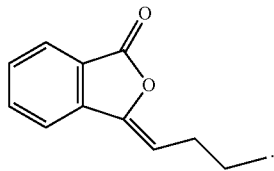

(I)

Another objective of this invention is to provide a method for inhibiting blood vessel stenosis in a subject, comprising administrating to the subject an effective amount of an *Anglicae Sinensis* extract comprising the aforesaid compound of formula (I).

Yet a further objective of this invention is to provide a pharmaceutical composition for inhibiting blood vessel stenosis, comprising an effective amount of an active ingredient selected from a group consisting of the aforesaid compound of formula (I), a pharmaceutically acceptable salt of the compound, a pharmaceutically acceptable ester of the compound, and combination thereof.

Still another objective of this invention is to provide an *Anglicae Sinensis* extract for inhibiting blood vessel stenosis, comprising the aforesaid compound of formula (I).

This invention also provides the use of the compound of formula (I) or a pharmaceutically acceptable salt or ester thereof in the manufacture of a medicament for inhibiting blood vessel stenosis.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1A:
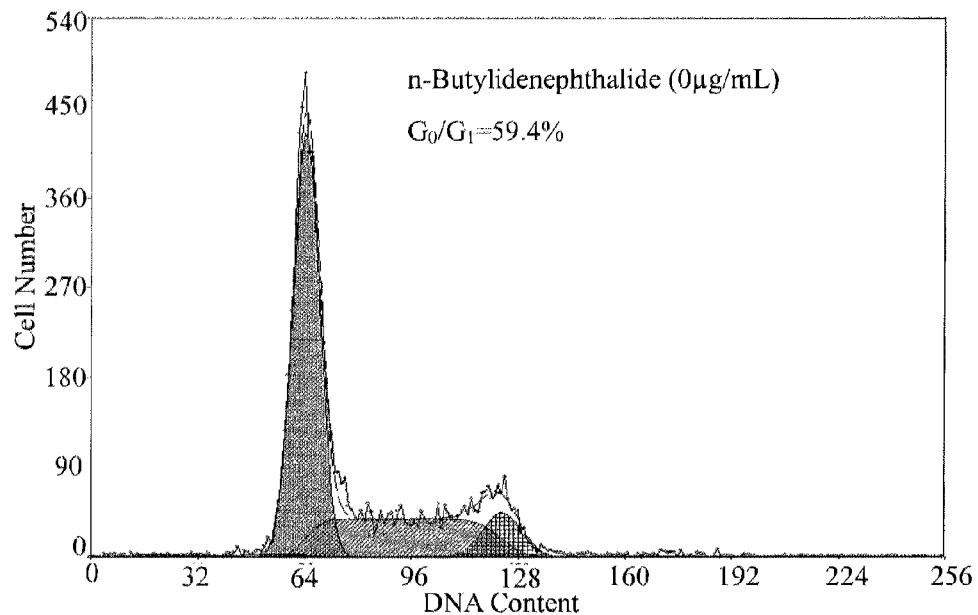
FIGS. 1A to 1C are flow cytometry analysis diagrams showing the percentage of a rat aortic smooth muscle cell line A7r5 in the cell cycle.
Figure 1B:
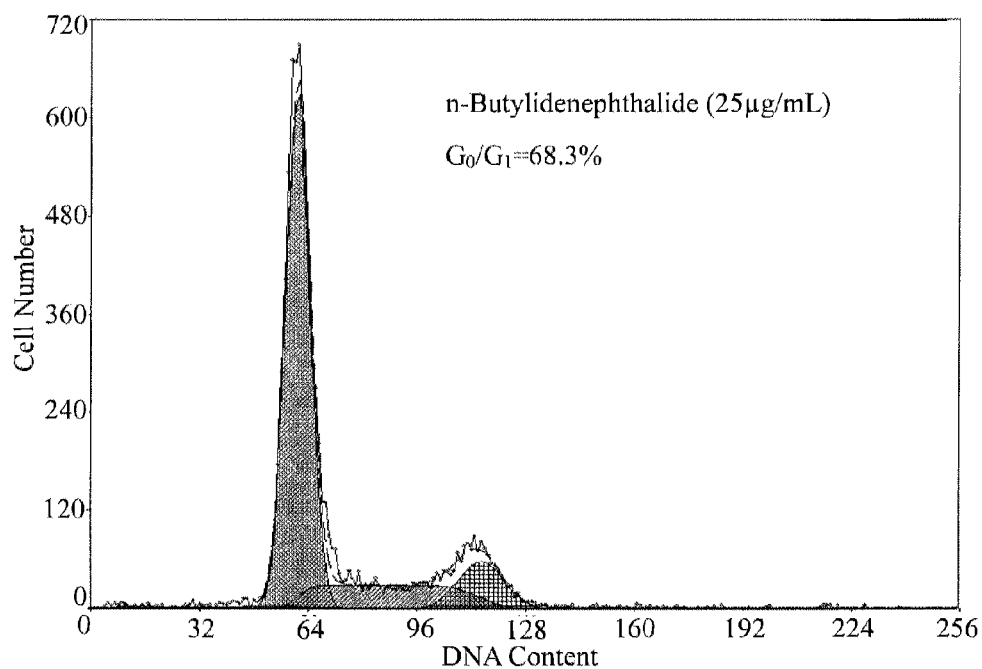
Figure 1C:
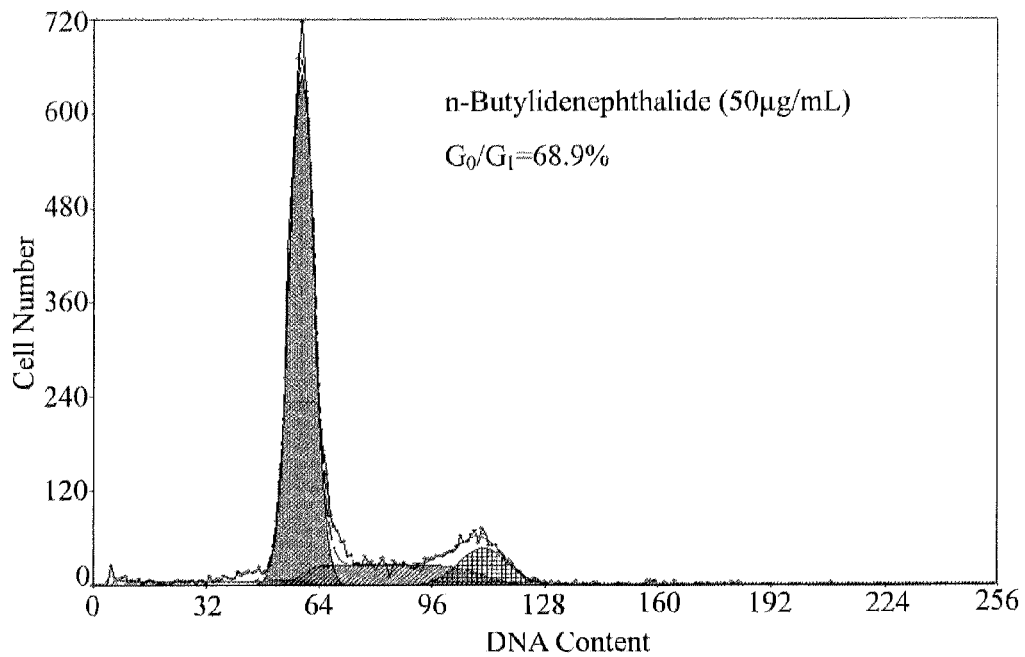

Unless otherwise stated herein, the terms "a (an)", "the" or the like used in this specification (especially in the Claims hereinafter) shall be understood to encompass both the singular form and the plural form.

As described above, because the effect of cardiovascular disease treatment by the use of drugs is relatively slow and limited, surgery is generally required to assist the treatment. However, the blood vessel can be injured by the implementation of the surgery and the related device, which promotes the proliferation of smooth muscle cells, leading to blood vessel restenosis and exacerbation of the condition. The inventors of the present invention had researched and found that an n-butylidenephthalide (abbreviated as "n-BP" or "bdph") compound can effectively inhibit the smooth muscle cell growth in the animal body, and further inhibit blood vessel stenosis. Therefore, the present invention provides a method for inhibiting blood vessel stenosis in a subject, comprising administrating to the subject an effective amount of an active ingredient selected from a group consisting of a compound of formula (I), a pharmaceutically acceptable salt of the compound, a pharmaceutically acceptable ester of the compound, and combinations thereof:

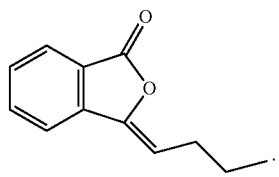

(I)

The compound of formula (I) is n-butylidenephthalide. Preferably, the active ingredient in the method of the present invention is the compound of formula (I).

As illustrated in the following examples, the carotid artery of an animal was damaged by surgery to induce the proliferation of smooth muscle cells of the blood vessel intimal layer, and then the animal was administrated with n-butylidenephthalide to achieve the effect of inhibiting blood vessel stenosis. Therefore, the method of the present invention not only can be carried out solely to treat cardiovascular disease, but also can be used together with surgery to inhibit or treat blood vessel restenosis induced by the surgery (e.g., stent implantation). Patients can be administrated (e.g., by oral intake) with the active ingredient in the present invention before stent implantation and/or balloon angioplasty to carry out general medicinal treatment to prevent the proliferation of smooth muscle cells in the blood vessel intimal layer in advance. Alternatively, after the surgery, the patients can be administrated (e.g., by oral intake) with the active ingredient in the present invention to inhibit the blood vessel restenosis induced by the surgery. In an embodiment, the active ingredient in the present invention can be coated onto the surface of the stent or balloon. The stent implantation or balloon angioplasty is then carried out to directly inhibit the proliferation of smooth muscle cells at the vascular stenosis site (i.e., the site where a stent or a balloon is placed) within the body.

Because the method of the present invention has the above mentioned effect, it can be used to treat atherosclerosis, especially to treat coronary atherosclerosis.

It has been found that n-butylidenephthalide of formula (I) is present in the extract of *Angelicae Sinesis*. Therefore, the present invention also relates to a method for inhibiting blood vessel stenosis in a subject, comprising administrating to the subject an effective amount of an *Angelicae Sinesis* extract comprising the compound of formula (I):

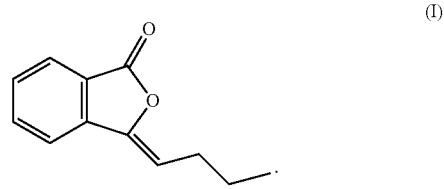

(I)

Because the compound of formula (I) has the effect of inhibiting blood vessel restenosis induced by surgery, the method using the *Angelicae Sinesis* extract of the present invention not only can be used alone to carry out the general treatment of cardiovascular disease, but also can be used in conjunction with surgery to inhibit blood vessel restenosis. Therefore, patients can be administrated (e.g., by oral intake) with the *Angelicae Sinesis* extract in the present invention before or after the stent implantation and/or balloon angioplasty. In an embodiment, the *Angelicae Sinesis* extract in the present invention can be coated onto the surface of the stent or balloon. Stent implantation or balloon angioplasty is then carried out to directly inhibit the proliferation of smooth muscle cells at the vascular stenosis site (i.e., the site where a stent or balloon is placed) within the body. The method using the *Angelicae Sinesis* extract of the present invention can be used to treat atherosclerosis, and particularly can be used to treat coronary atherosclerosis. The *Angelicae Sinesis* extract can be administrated as a medicament.

The present invention also provides a pharmaceutical composition for inhibiting blood vessel stenosis, comprising an effective amount of an active ingredient selected from a group consisting of the compound of formula (I), a pharmaceutically acceptable salt of the compound, a pharmaceutically acceptable ester of the compound, and combination thereof.

The present invention also provides an *Anglicae Sinensis* extract for inhibiting blood vessel stenosis, comprising the compound of formula (I).

The present invention further provides the use of the compound of formula (I) or a pharmaceutically acceptable salt or ester thereof in the manufacture of a medicament for inhibiting blood vessel stenosis. The medicament can be used to treat atherosclerosis, particularly to treat coronary atherosclerosis. In addition, the medicament can be used before or after stent implantation and/or balloon angioplasty to inhibit blood vessel stenosis.

The compound of formula (I) can be purchased from the market (CAS No. 551-08-6) or obtained from extraction and purification of *Angelicae Sinesis*. For example, the root and stem of *Angelicae Sinesis* can be extracted by acetone, and then by chloroform or hexane. Finally, high performance liquid chromatography (HPLC) was used to purify the compound of formula (I) (see US Patent Publication No. 2007/0134351 A1, which is incorporated hereinto by reference).

The pharmaceutical composition of the present invention can be applied by any suitable approach, for example, but not limited thereby, oral, subcutaneous, or intravenous administration. The pharmaceutical composition of the present invention can be applied alone or in conjunction with medicinal adjuvant in veterinary and human medicine.

With respect to a medicament suitable for oral administration, for example, the pharmaceutical composition of the present invention may comprise an adjuvant that would not adversely affect the activity of the compound of formula (I), for example, solvents, oily solvents, diluents, stabilizers, absorption retarders, disintegrants, emulsifiers, adhesives, lubricants, moisture absorbents, etc. For example, the solvents can be selected from water and a sucrose solution; the diluents can be selected from lactose, starch, and microcrystalline cellulose; the absorption retarders can be selected from chitosan and glucosaminoglycan; the lubricants can be selected from magnesium carbonate; the oily solvents can be selected from plant or animal oils, such as olive oil, sunflower oil, cod liver oil, etc. The pharmaceutical composition can be prepared in any suitable oral dosage form by known methods, for example, tablets, capsules, granules, pulvis, fluid extracts, solutions, syrups, suspensions, emulsions, tinctures, etc.

As for the dosage form suitable for subcutaneous or intravenous administration, the pharmaceutical composition of the present invention may comprise one or more ingredients like solubilizers, emulsifiers, and other adjuvant to form an intravenous fluid injection, an intravenous emulsion injection, an injection solution, a dry powder injection, a suspension injection, a dry powder suspension injection, etc. Solvents that can be used include water, a physiological saline solution, alcohols (for example, ethanol, propanol, or glycerol etc), a sugar solution (for example, a glucose solution or a mannose solution), or combinations thereof.

The pharmaceutical composition of the present invention may optionally further comprise additives like flavoring agents, toners, and coloring agents to improve the oral and visual sensation during the administration of the medicament. A reasonable amount of preservatives, antiseptic agents, antibacterial agents, anti-fungal agents, etc, can be added to improve the storability of the medicament.

Furthermore, the pharmaceutical composition of the present invention may optionally comprise one or ore other active components to enhance the efficacy of the pharmaceutical composition of the present invention or increase the flexibility for manufacturing formulations. For example, the pharmaceutical composition of the present invention may comprise one or more following active components: anticoagulants (such as Coumadin), antiplatelet agents (such as aspirin), vasodilators (such as Isordil), hypolipidemic drugs (such as Statins), other active components, etc, as long as the other active components do not have adverse effects to the compound of formula (I).

The pharmaceutical composition of the present invention can be administered with different dosage frequencies, such as once per day, multiple times a day, or once per multiple days, based on the requirement of the subject. For example, when the composition is used to treat atherosclerosis in the human body, the active ingredient is administrated at a daily dosage of about 50 mg/kg-body weight to about 500 mg/kg-body weight, based on the compound of formula (I), wherein the unit "mg/kg-body weight" refers to the dosage required for the subject per kg-body weight. Preferably, the active ingredient is administrated at a daily dosage of about 100 mg/kg-body weight to about 400 mg/kg-body weight, based on the compound of formula (I). However, for patients with more severe condition, the dosage can be increased to several or several tens of times depending on practical conditions.

The detailed technology and preferred embodiments implemented for the present invention are described in the following paragraphs accompanying the appended drawings for people skilled in this field to well appreciate the features of the claimed invention.

EXAMPLES

Experiment A

Inhibiting Proliferation of Smooth Muscle Cells—Cell Cycle Analysis

A rat aortic smooth muscle cell line A7r5 was used to carry out the present experiment. A Dulbecco's modified Eagle's medium (DMEM, purchased from Biowest) was used as a general culture medium. The medium was added with 4 mM of L-glutamine, 1.5 g/L sodium bicarbonate, 4.5 g/L glucose, and 10 wt % fetal bovine serum. The A7r5 smooth muscle cells were cultured in a 75 $cm^2$ petri dish, and 12 mL of the culture medium was added thereinto. The cells were placed and incubated in a cell incubator containing 5 vol % of carbon dioxide at 37° C. After the dish was fully covered by the grown cells, the medium was replaced once every 3 days, and 0.5 wt % trypsin was used for subculture.

In addition, a culture medium containing n-butylidenephthalide was prepared. Herein, n-butylidenephthalide was dissolved in dimethyl sulfoxide (purchased from Sigma), and solutions with n-butylidenephthalide concentrations of 0, 25, 50, 100, 150, and 200 mg/mL were prepared, and the solutions were stored at −20° C. When used to prepare a medium, the solutions were diluted by 1000 times with the general culture medium used for incubating smooth muscle cells to prepare a culture medium containing 0, 25, 50, 100, 150, or 200 μg/mL of n-butylidenephthalide.

An inhibition test on the cell cycle progression of smooth muscle cells was carried out. Because the cellular DNA content is different in each cell cycle phase, the amount of DNA can be used to evaluate the cell cycle phase in which the cell proceeds. In another aspect, because propidium iodide can bind to DNA, and it can emit red fluorescent light with a wavelength of 625 nm after being excited by light with a wavelength of 488 nm, thus, propidium iodide was used as a fluorescent staining agent in the present experiment, and the red fluorescent intensity represented the amount of DNA, thereby determining which phase the cell was in during the cell cycle.

The rat aortic smooth muscle cell line A7r5 was inoculated in a 6-hole culture dish (density: $1\times10^5$ cells/hole). After the cells were cultured for 24 hours, the medium was replaced by a medium containing n-butylidenephthalide with a concentration of 0, 25, or 50 μg/mL to culture the smooth muscle cells. After another 24 hours, the cells were fixed with 70 vol % alcohol, and a phosphate buffer solution (PBS) was used to rinse the cells. Finally, propidium iodide (a solution containing 955 μL 1×PBS, 5 μL Triton X-100 (0.5 wt %, purchased from Sigma), 20 μL RNase A (10 mg/mL, purchased from Sigma), and 20 μL propidium iodide (1 mg/mL, purchased from Sigma)) was used to stain the cells for 15 minutes. Then, a flow cytometry (FC500, Beckman) was used to scan and collect 10,000 cells. Multicycle for Windows software (Phoenix Flow Systems) was used to analyze cellular cell cycle. The results are shown in Table 1, FIGS. 1A and 2.

TABLE 1

| Cell cycle | Concentration of n-butylidenephthalide (μg/mL) | Ratio (%) |
|---|---|---|
| G0/G1 | 0 | 59.4 +/− 2.4 |
|  | 25 | 68.33 +/− 0.05 |
|  | 50 | 68.86 +/− 5.2 |
| G2/M | 0 | 13.43 +/− 0.4 |
|  | 25 | 11.3 +/− 1.25 |
|  | 50 | 12.1 +/− 1.15 |
| S | 0 | 27.16 +/− 2.02 |
|  | 25 | 20.33 +/− 2.05 |
|  | 50 | 19.00 +/− 4.3 |

Figure 2:
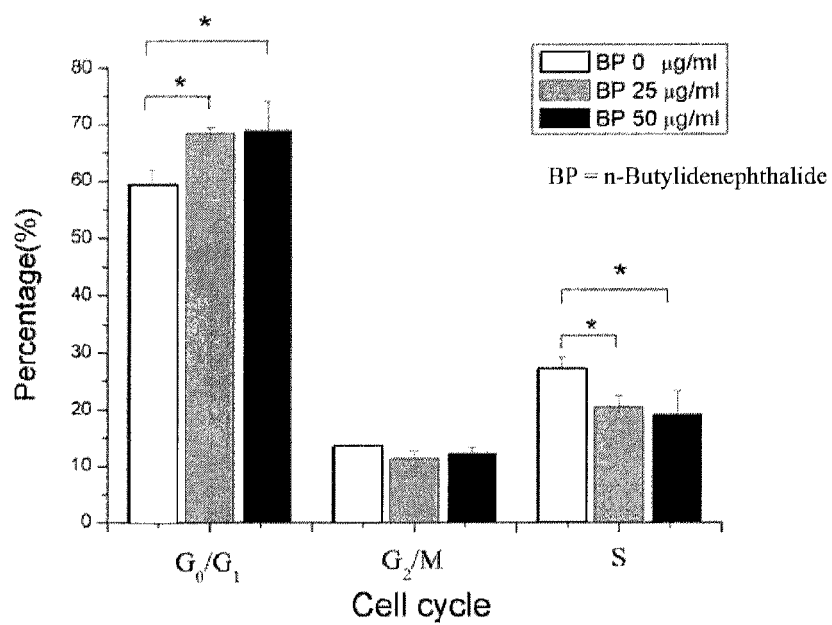
FIG. 2 is a statistical bar diagram showing the percentage of the rat aortic smooth muscle cell line A7r5 in the cell cycle.

As shown in Table 1, FIGS. 1A and 2, the ratio of smooth muscle cells occupied in G0/G1 phase increased from 59.4% (without drug treatment) to 68.9% (drug concentration: 50 μg/mL) as the concentration of n-butylidenephthalide increased, whereas the S phase ratio decreased from 27.2% (without drug treatment) to 19.0% (drug concentration: 50 μg/mL). The result illustrated that n-butylidenephthalide would stagnate the smooth muscle cells in the G0/G1 phase, which makes the cell ratio increase in G0/G1 phase but decrease in S phase, thereby, stopping the proliferation of the smooth muscle cells.

Experiment B

Inhibiting Proliferation of Smooth Muscle Cells—Cell Counting Analysis

The rat aortic smooth muscle cell line A7r5 was inoculated in a 6-hole culture dish (density: $1 \times 10^5$ cells/hole). After the cells were cultured for 24 hours, the medium was replaced by a medium containing n-butylidenephthalide with a concentration of 0, 25, 50, 100, 150, or 200 μg/mL to culture the smooth muscle cells. After another 48 hours, the cells were observed by an inverted microscope, and the cells were detached by 0.5 wt % trypsin. Then, 20 μL of the cell suspension was taken and mixed evenly with 20 μL trypan blue, and finally, 10 μL of the mixture was collected and added onto a blood cell counting plate. The cell number was counted by a microscope under 100× magnifications to evaluate the inhibition of n-butylidenephthalide on the growth of the smooth muscle cells. The results are shown in Table 2, FIGS. 3 and 4.

TABLE 2

| Concentration of n-butylidenephthalide (μg/mL) | Growth rate (%) |
|---|---|
| 0 | 1.00 +/− 0.16 |
| 25 | 0.56 +/− 0.06 |
| 50 | 0.32 +/− 0.04 |
| 100 | 0.25 +/− 0.03 |
| 150 | 0.12 +/− 0.04 |
| 200 | 0.10 +/− 0.02 |

Figure 3:
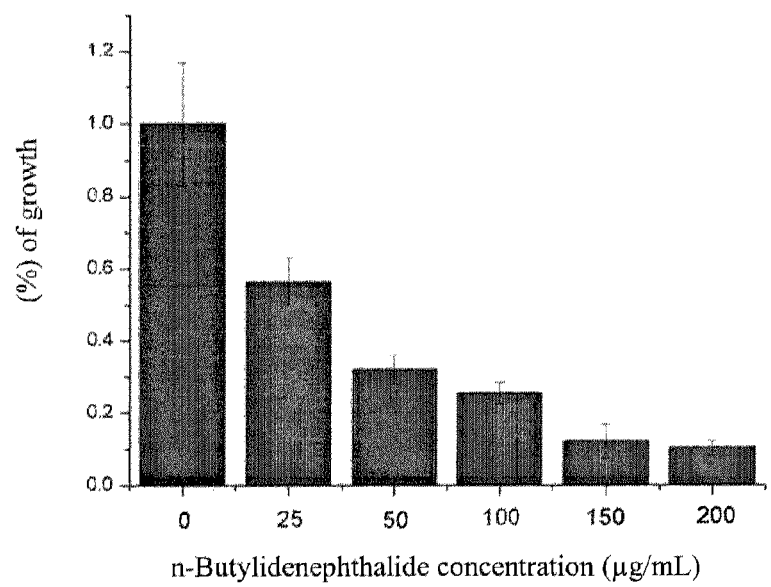
FIG. 3 is a statistical bar diagram showing the inhibition of n-butylidenephthalide on the growth of the rat aortic smooth muscle cell line A7r5.
Figure 4:
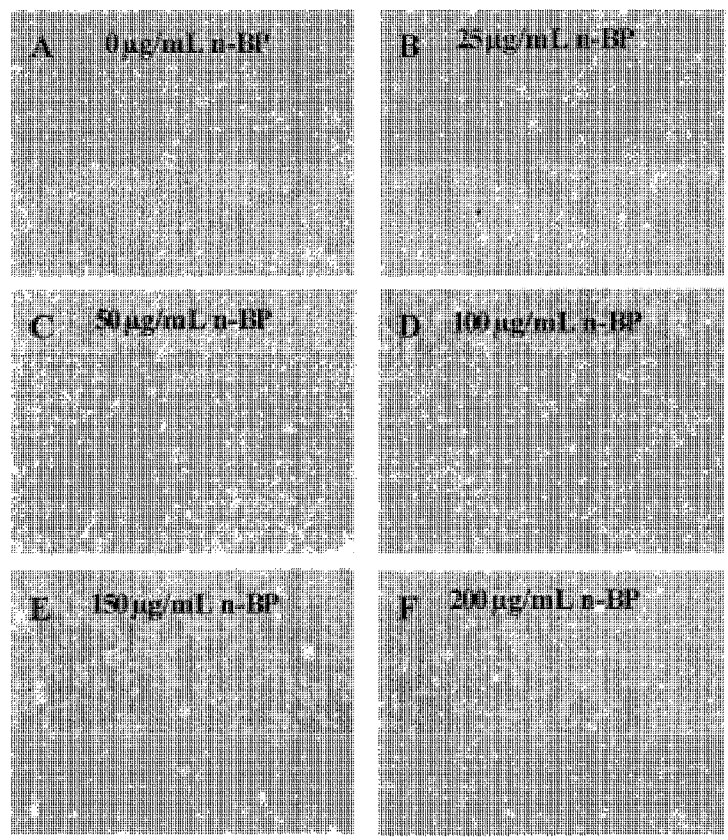
FIG. 4 is a microscopic diagram showing the inhibition of n-butylidenephthalide on the growth of the rat aortic smooth muscle cell line A7r5.

As shown in Table 2, FIGS. 3 and 4, the density, number, and growth rate of the smooth muscle cells all significantly decreased as the concentration of n-butylidenephthalide increased, and the smooth muscle cell growth was significantly inhibited to a inhibition rate of 43.6% at the concentration of 25 μg/mL ($IC_{50}$=27.0 μg/mL (143.4 μM)). Therefore, n-butylidenephthalide can inhibit the proliferation of the smooth muscle cells.

Experiment C

Animal Test—Carotid Artery Injury Induced Blood Vessel Stenosis

Sprague-Dawley (SD) rats (purchased from BioLasco Taiwan Co. Ltd, Taipei) were used in the present experiment to carry out the animal test. The rats were bred in an environment with 12 hours light, followed by 12 hours dark, and fed to 10-weeks old (body weight: about 300 to 400 g). Then, carotid artery injury surgery and the following experiments were carried out. The present experiment followed the Animal Protection Act and the provisions of Animal Management Committee of National Dong Hwa University.

The SD rat was anesthetized by 320 mg/kg-body-weight chloral hydrate (purchased from Fluka), and then the abdominal area was faced upwards, and the limbs were fixed with a breathable tape on a surgery plate. The Casscells' method (Casscells et al., Migration of smooth muscle and endothelial cells. Critical events in restenosis, *Circulation*, 1992; 86; 723-729, which is incorporated hereinto by reference) was used to carry out the carotid artery injury surgery. First, the skin of the rat was cut open with a scissor from the midline of the neck jaw to the chest area, and then the connective tissue at the right side of the rat neck was separated from the muscle layer to expose the blood vessel next to the trachea, and the blood vessel is the common carotid artery. The right side common carotid artery, internal carotid artery, and external carotid artery were separated, and the connective tissue at the junction of these three blood vessels was completely striped. Then, the external carotid artery was tied up with a 2/0 sized silk thread, and the common carotid artery was clipped by a vascular clip to avoid heavy bleeding. A gap was made by cutting the external carotid artery with a microscopic scissor, and a balloon catheter (Cather French Size 2F, purchased from Edwards Lifescience) was implanted through the gap. The balloon catheter was inserted 5 cm into the common carotid artery, and 0.2 mL of a physiological saline solution was filled into the balloon catheter to expend the catheter. Then, the balloon catheter was pulled out to the gap of the external carotid artery, and the physiological saline solution was drawn out from the balloon catheter. After the common carotid artery was injured repeatedly for three times by this method, the gap of the external carotid artery and the bifurcation point between the external carotid artery and the common carotid artery were tied up with a 2/0 sized silk thread. Finally, the wound of the rat was stitched up and spread with an iodine solution. After the rat woke up, the carotid artery injury surgery was completed.

Two weeks after the carotid artery injury surgery, the rat was sacrificed with excess chloral hydrate (640 mg/kg-body weight). PBS (300 mL) was injected into the left ventricle of the rat using the heart perfusion method and flowed out from the right ventricle through systemic circulation. Neutral formalin (200 mL, 10 vol %) was injected into the left ventricle of the rat to immobilize the whole body tissue. The common carotid artery immobilized by formalin was removed and soaked in a 10 vol % neutral formalin solution.

The common carotid artery was divided into four sections and labeled with A, B, C, and D from the head to the heart. Each section was 4 mm in length and was placed in an embedding cassette, and then an automatic tissue processor (purchased from Sakura) was used to process the tissue. The process procedure was 1 hour in a 10 vol % formalin solution, 30 minutes in water, 1 hour in 80 vol % alcohol, 3 hours in 95 vol % alcohol, 4 hours in 100 vol % alcohol, 3 hours in xylene, and 3 hours in paraffin. After the tissue process procedure was completed, the tissue was wrapped by paraffin, and the tissue biopsy was carried out by a slicer (purchased from Lica) with a cut of 8 μm thickness. Immunohistochemical stain and H&E stain on the biopsy were carried out. Motic software was then used to analyze and calculate the increased area of the blood vessel intimal layer to evaluate the proliferation of the smooth muscle cells in the blood vessel of the rat. In the immunohistochemical stain, an anti-α-smooth muscle actin kit (purchased from Sigma) was used to provide a primary antibody to bind α-smooth muscle actin in the blood vessel, and then a secondary antibody with biotin was used to bind the primary antibody, and finally, streptavidin with peroxidase was used to bind the secondary antibody. The rat tissue biopsy was stained to confirm the position of the α-smooth muscle actin and the smooth muscle cells, and the evaluation was made accordingly. The results of H&E stain and immunohistochemical stain are shown in FIG. 5.

Figure 5:
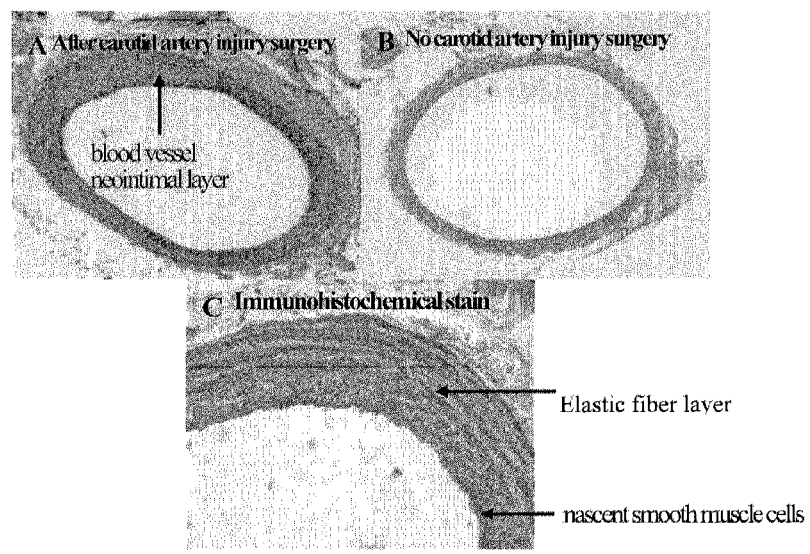
FIG. 5 is a stained histological diagram showing the carotid artery of a Sprague-Dawley (SD) rat.
Figure 6:
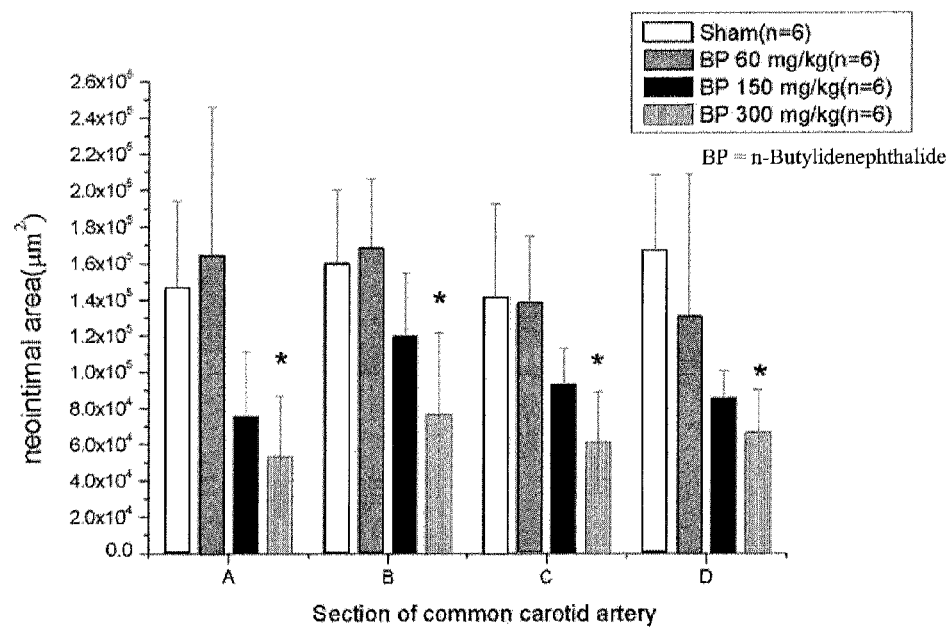
FIG. 6 is a statistical bar diagram showing the increased area of the blood vessel neointimal layer in the carotid artery of the SD rat.
Figure 7:
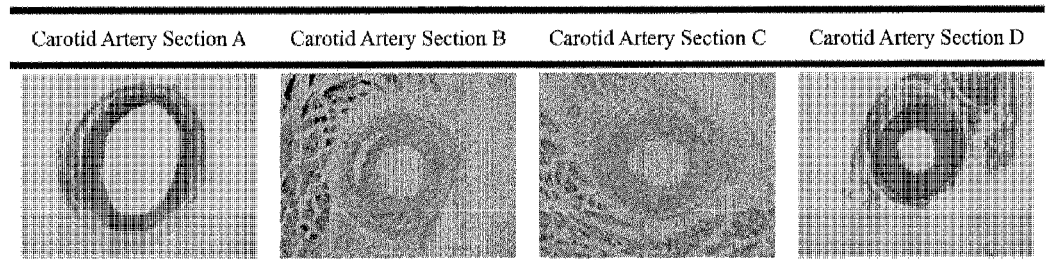
FIG. 7 is an H&E-stained histological diagram showing the carotid artery of the SD rat.
Figure 7:
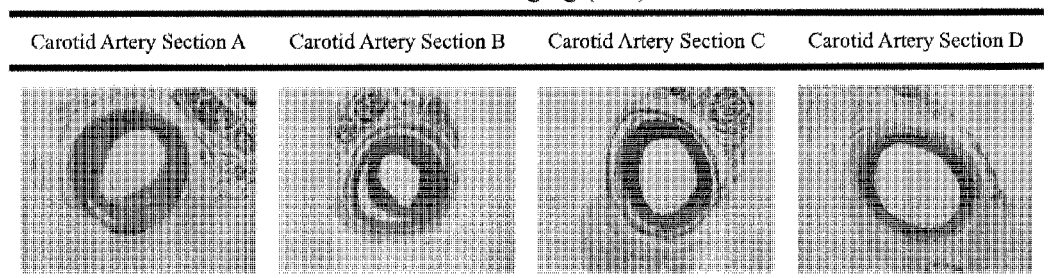
Figure 7:
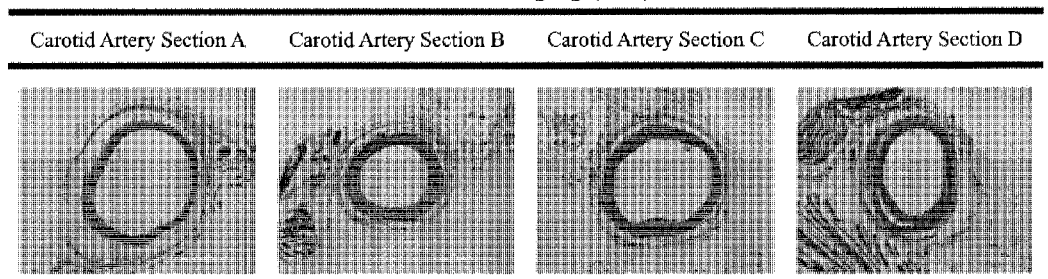
Figure 7:
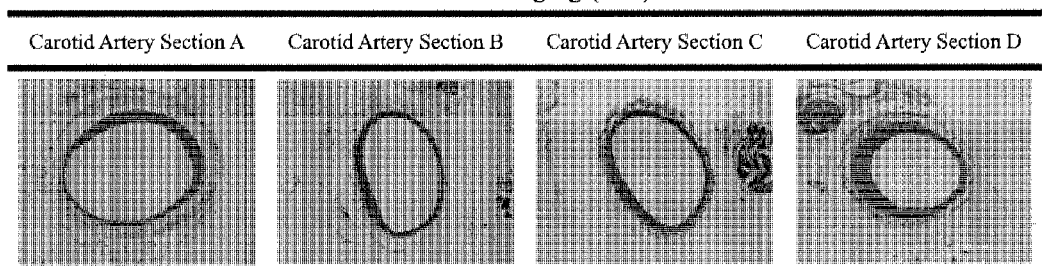
Figure 8:
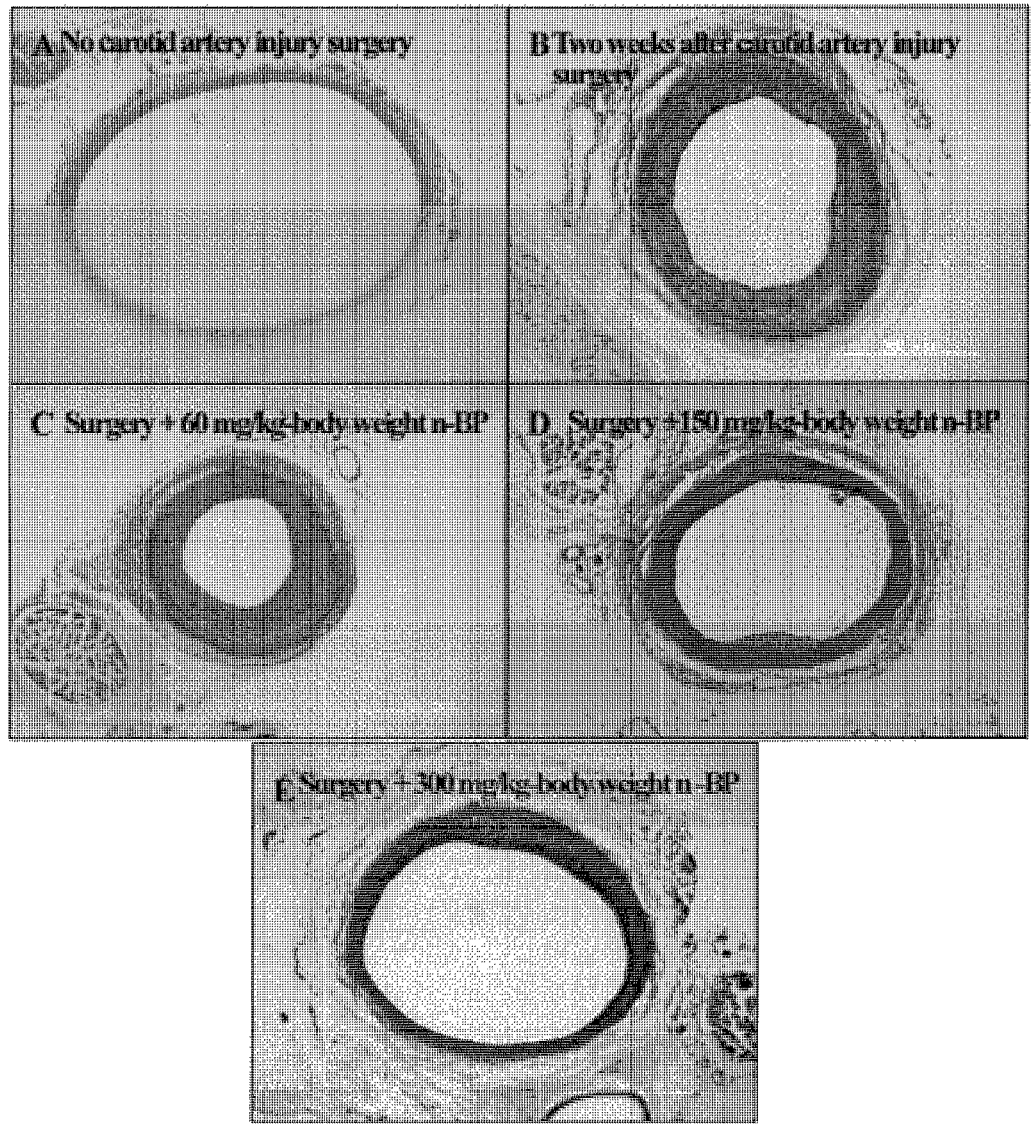
FIG. 8 is an H&E-stained histological diagram showing the carotid artery of the SD rat.
Figure 9:
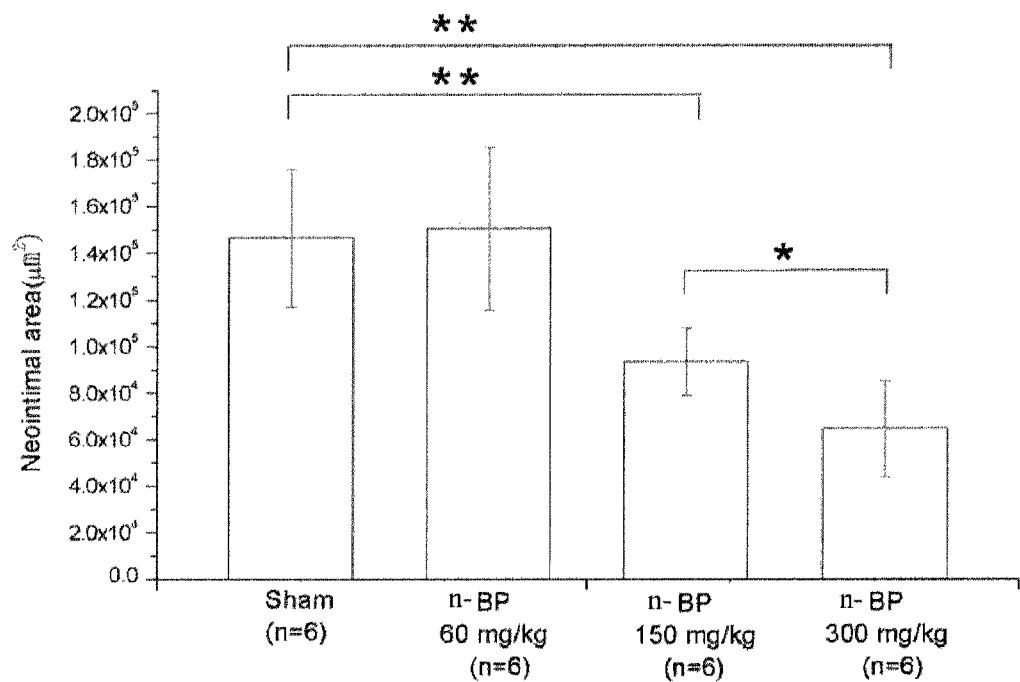
FIG. 9 is a statistical bar diagram showing the increased area of the blood vessel neointimal layer in the carotid artery of the SD rat.
Figure 10:
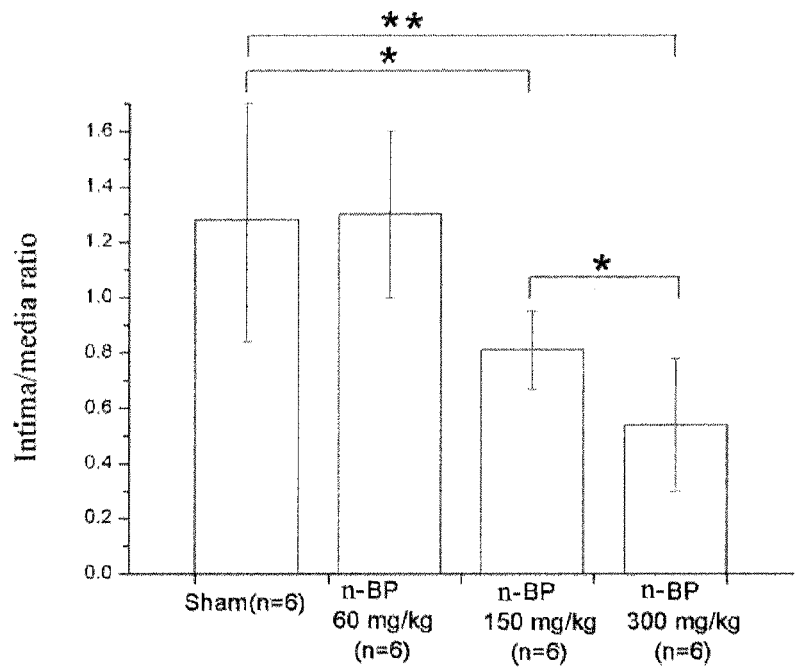
FIG. 10 is a statistical bar diagram showing the ratio of the increased area of the blood vessel neointimal layer to the middle layer area in the carotid artery of the SD rat.

As shown in FIG. 5, the carotid artery injury surgery can increase the average area of the rat's carotid artery to 146,000±29,000 μm$^2$, indicating that the carotid artery injury surgery can induce the thickening of the blood vessel neointimal layer and cause blood vessel stenosis.

Experiment D

Animal Test—Treatment of Carotid Artery Injury Induced Blood Stenosis

After carotid artery injury surgery was carried out on the SD rats, they were randomly grouped into four groups. There were six rats in each group, and the rats were dosed with medicine through abdominal injection, wherein the first group was a sham group; the second group was administrated with 60 mg/kg-body weight of n-butylidenephthalide by abdominal injection; the third group was administrated with 150 mg/kg-body weight of n-butylidenephthalide by abdominal injection; and the fourth group was administrated with 300 mg/kg-body weight of n-butylidenephthalide by abdominal injection. The administration time points were the $1^{st}$, $3^{rd}$, $5^{th}$, $7^{th}$, $9^{th}$, and $11^{th}$ day after the carotid artery injury surgery. At the $14^{th}$ day, the rats were sacrificed with excess chloral hydrate, and a 10 vol % neutral formalin solution was injected into the hearts of the rats to immobilize the hearts. The common carotid artery was removed and divided into four sections and labeled as A, B, C, and D, and then the tissue was processed and wrapped with paraffin. Finally, the biopsy, H&E stain, and immunohistochemical stain were carried out. Motic software was used to analyze and calculate the increased area of the blood vessel intimal layer and the degree of stenosis of the blood vessel. The results are shown in Tables 3 to 6 and FIGS. 6 to 10.

TABLE 3

| Carotid artery section | n-Butylidenephthalide dosage (mg/kg-body weight) | Blood vessel neointimal layer area (μm$^2$) |
|---|---|---|
| Section A | 0 (Sham) | 145650 +/− 48589 |
| | 60 | 164528 +/− 81467 |
| | 150 | 75272 +/− 36346 |
| | 300 | 53118 +/− 33403 |
| Section B | 0 (Sham) | 160118 +/− 39959 |
| | 60 | 168355 +/− 37686 |
| | 150 | 119827 +/− 35005 |
| | 300 | 76551 +/− 45327 |
| Section C | 0 (Sham) | 141312 +/− 51469 |
| | 60 | 138260 +/− 36681 |
| | 150 | 93111 +/− 19875 |
| | 300 | 61150 +/− 27899 |
| Section D | 0 (Sham) | 166005 +/− 42394 |
| | 60 | 130852 +/− 77915 |
| | 150 | 85273 +/− 15262 |
| | 300 | 66654 +/− 23434 |

TABLE 4

| n-Butylidenephthalide dosage (mg/kg-body weight) | Blood vessel neointimal layer area (μm$^2$) |
|---|---|
| 0 (Sham) | 146347 +/− 29296 |
| 60 | 150499 +/− 34951 |
| 150 | 93371 +/− 14693 ** |
| 300 | 64368 +/− 20641 ** |

**: $P < 0.01$

TABLE 5

| n-Butylidenephthalide dosage (mg/kg-body weight) | Blood vessel neointimal layer area /middle layer area (intima/media ratio) |
|---|---|
| 0 (Sham) | 1.28 +/− 0.44 |
| 60 | 1.3 +/− 0.3 |
| 150 | 0.81 +/− 0.14* |
| 300 | 0.54 +/− 0.24** |

*$P < 0.05$,
**$P < 0.01$

TABLE 6

| | The percentage of blood stenosis (%) | | | |
|---|---|---|---|---|
| Increased area (μm$^2$) | Sham (n = 6) | n-Butylidenephthalide 60 mg/kg-body weight (n = 6) | n-Butylidenephthalide 150 mg/kg-body weight (n = 6) | n-Butylidenephthalide 300 mg/kg-body weight (n = 6) |
| 0~50,000 | 0 | 0 | 0 | 2 (33.3%) |
| 50,000~100,000 | 0 | 0 | 3 (50%) | 3 (50.0%) |
| 100,000~150,000 | 4 (66.7%) | 4 (66.7%) | 3 (50%) | 1 (16.7%) |
| Above 150,000 | 2 (33.3%) | 2 (33.3%) | 0 | 0 |

Note:

TABLE 6-continued

| | The percentage of blood stenosis (%) | | | |
|---|---|---|---|---|
| Increased area ($\mu m^2$) | Sham (n = 6) | n-Butylidenephthalide 60 mg/kg-body weight (n = 6) | n-Butylidenephthalide 150 mg/kg-body weight (n = 6) | n-Butylidenephthalide 300 mg/kg-body weight (n = 6) |

The number within the table represents the number of the rats that achieved the increased level as indicated. The percentage in the bracket represents the proportion of the rats whose increased area of the blood vessel neointimal layer reached to the level as indicated in each experimental group.

As shown in Tables 3 to 6 and FIGS. 6 to 10, n-butylidenephthalide can inhibit the thickening of the rat's blood vessel neointimal layer, and such inhibition was proportional to the n-butylidenephthalide dosage. When the rats were administrated with 150 and 300 mg/kg-body weight n-butylidenephthalide, the blood vessel stenosis can significantly be inhibited, whereas there was no significant inhibition effect in the sham group and the rats administrated with 60 mg/kg-body weight n-butylidenephthalide.

In addition, compared with the shame group, the n-butylidenephthalide dosages of 150 and 300 mg/kg-body weight can remarkably inhibit the blood vessel stenosis to 36.3% and 56.2%, respectively. Moreover, if blood vessel neointimal layer area/blood vessel middle layer area (i.e., intima/media ratio) was considered, then, the blood vessel stenosis was inhibited to 36.7% and 57.8%, respectively.

As shown in Table 6, the rats in each group were classified according to the level of the increased area of the blood vessel neointimal layer. The proportion of the rats whose increased area of the blood vessel neointimal layer was under $1 \times 10^5$ $\mu m^2$ in each group was: the sham group: 0%; 60 mg/kg-body weight dosage: 0%; 150 mg/kg-body weight dosage: 50%; and 300 mg/kg-body weight dosage: 83.3%. This showed that there was a higher proportion of the rats whose increased area of the blood vessel neointimal layer decreased as n-butylidenephthalide dosage increased.

The results from Experiment C and Experiment D had proven that n-butylidenephthalide can indeed inhibit the thickening of the blood vessel neointimal layer within the animal body to achieve the inhibition effect on blood vessel stenosis. Therefore, n-butylidenephthalide can be used to treat cardiovascular disease or inhibit the side effect of blood vessel restenosis caused by surgery.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for inhibiting blood vessel stenosis in a subject, comprising administrating to the subject an effective amount of an active ingredient selected from the group consisting of a compound of formula (I), a pharmaceutically acceptable salt of the compound, a pharmaceutically acceptable ester of the compound, and combinations thereof:

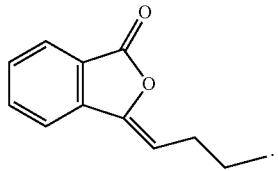

(I)

2. The method as claimed in claim 1, wherein the active ingredient is the compound of formula (I).

3. The method as claimed in claim 1, wherein the active ingredient is administered by oral intake before or after a surgery selected from the group consisting of stent implantation, balloon angioplasty, and a combination thereof.

4. The method as claimed in claim 1, which is used for treating restenosis after a surgery of stent implantation and atherosclerosis.

5. The method as claimed in claim 1, wherein the active ingredient is administered at a daily dosage of about 50 mg/kg-body weight to about 500 mg/kg-body weight.

6. The method as claimed in claim 5, wherein the active ingredient is administered at a daily dosage of about 100 mg/kg-body weight to about 400 mg/kg-body weight.

7. A method for inhibiting blood vessel stenosis in a subject, comprising administrating to the subject an effective amount of an *Angelicae Sinensis* extract comprising a compound of formula (I):

(I)

8. The method as claimed in claim 7, wherein the extract is administrated by oral intake before or after a surgery selected from the group consisting of stent implantation, balloon angioplasty, and a combination thereof.

9. The method as claimed in claim 7, which is used for treating atherosclerosis.

10. The method as claimed in claim 7, wherein the extract is administrated at a daily dosage of about 50 mg/kg-body weight to about 500 mg/kg-body weight, based on the total weight of the compound of formula (I).

11. The method as claimed in claim 10, wherein the extract is administrated at a daily dosage of about 100 mg/kg-body weight to about 400 mg/kg-body weight, based on the total weight of the compound of formula (I).

12. The method as claimed in claim 7, wherein the extract is administrated as a medicament.

* * * * *